| United States Patent [19] | [11] Patent Number: 4,979,957 |
| Hodorek | [45] Date of Patent: Dec. 25, 1990 |

[54] TEXTURED PROSTHETIC IMPLANT

[75] Inventor: Robert A. Hodorek, Warsaw, Ind.

[73] Assignee: Zimmer, Inc., Warsaw, Ind.

[21] Appl. No.: 405,260

[22] Filed: Sep. 11, 1989

[51] Int. Cl.⁵ .............................................. A61F 2/38
[52] U.S. Cl. ........................................ 623/20; 623/16
[58] Field of Search ................... 623/16, 18, 19, 20, 623/22, 23

[56] References Cited

U.S. PATENT DOCUMENTS

| D. 232,004 | 7/1974 | Amstutz | D24/99 |
| D. 232,005 | 7/1974 | Farling | D24/99 |
| D. 245,259 | 8/1977 | Shen | D24/33 |
| D. 276,463 | 11/1984 | Hamm | D24/33 |
| 3,728,742 | 4/1973 | Averill et al. | 3/1 |
| 3,816,855 | 6/1974 | Saleh | 3/1 |
| 3,869,731 | 3/1975 | Waugh et al. | 3/1 |
| 4,081,866 | 4/1978 | Upshaw et al. | 3/1.911 |
| 4,158,894 | 6/1979 | Worrell | 3/1.91 |
| 4,209,861 | 7/1980 | Walker et al. | 3/1.911 |
| 4,215,439 | 8/1980 | Gold et al. | 3/1.911 |
| 4,240,162 | 12/1980 | Devas | 3/1.91 |
| 4,285,070 | 8/1981 | Averill | 3/1.911 |
| 4,309,778 | 1/1982 | Buechel et al. | 3/1.911 |
| 4,340,978 | 7/1982 | Buechel et al. | 3/1.911 |
| 4,344,192 | 7/1982 | Imbert | 3/1.91 |
| 4,353,135 | 10/1982 | Forte et al. | 3/1.911 |
| 4,470,158 | 9/1984 | Pappas et al. | 3/1.911 |
| 4,479,271 | 10/1984 | Bolesky et al. | 3/1.911 |
| 4,714,473 | 12/1987 | Bloebaum | 623/20 |
| 4,759,767 | 7/1988 | Lacey | 623/20 |
| 4,769,039 | 9/1988 | Horber | 623/20 |
| 4,865,603 | 9/1989 | Noiles | 623/18 |
| 4,883,490 | 11/1989 | Oh | 623/22 |

FOREIGN PATENT DOCUMENTS

| 0151724A1 | 8/1985 | European Pat. Off. |
| 0189253A2 | 7/1986 | European Pat. Off. |
| 2520055A1 | 11/1975 | Netherlands |
| WO89/06947 | 8/1989 | PCT Int'l Appl. |

OTHER PUBLICATIONS

Howmedica-PCA Total Knee Reconstructive Systems-JBJS, 10/86.
Howmedica-PCA Modular Total Knee System-JBJS, 09/88.
Howmedica-Kinematic II Total Knee System-JBJS 03/85.
Johnson & Johnson Orthopaedics-Press Fit Condylar Knee System-1988.
Johnson & Johnson Orthopaedics-PFC Total Knee System Long Stem-JBJS, 06/88.
Johnson & Johnson Orthopaedics-Press-Fit Condylar Total Knee System-JBJS, 12/86.
Richards-Tricon Total Knee System-JBJS, 09/88.
Richards-RMC Total Knee System-1978.
Richards-Tricon-P Cementless Tibial Component-1983.
Osteonics Corp.-Omnifit Total Knee System-1987.
Orthomet, Inc.-Orthomet PLUS Total Knee System-JBJS, 09/87.
Zimmer, Inc.-Insall/Burstein Total Knee System-1985.
Zimmer, Inc.-Universal Patellar Dome (p. A-183) and Patellar Component (p. A-200)-1987 Catalog.
Zimmer, Inc.-Geo-Patella/Geo-Tibial Total Knee System-1977.

(List continued on next page.)

*Primary Examiner*—David J. Isabella
*Attorney, Agent, or Firm*—Margaret L. Geringer

[57] ABSTRACT

A prosthetic implant which includes a top surface and an undersurface oppositely located therefrom. The undersurface includes a raised peripheral rim, a plurality of raised islands, and at least one raised rail all arranged in a pattern to create a textured undersurface. The raised portions are undercut. The arrangement of the raised portions is designed so that the bone cement which is used to secure the implant to the bone cell interlock securely to the undersurface to resist potential subsequent loosening of the implant.

22 Claims, 1 Drawing Sheet

OTHER PUBLICATIONS

Zimmer, Inc.-Miller/Galante Total Knee System-1986.
Allo Pro-GSB Knee Endoprosthesis-1982.
Allo Pro-GSB Knee Prosthesis System-JBJS, 04/88.
Biomet-Comp-2, A New Era in Patella Resurfacing-JBJS, 12/81.
DePuy-LCS Total Knee System-JBJS, 10/88.
DePuy-AMK Total Knee System-No Date Available.
DePuy-Synatomic Knee Femoral & Patellar Components-1984.
Dow Corning Wright-Pushing All the Wright Buttons-1988.
Dow Corning Wright-Whiteside Ortholoc II Total Condylar Knee System-1987.
Dow Corning Wright-Whiteside Ortholoc 11-C Total Condylar Knee System-1987.
Dow Corning Wright-Lacey Condylar Total Knee System-1983.
Howmedica-Kinemax Modular Total Knee System-JBJS, 10/88.

U.S. Patent
Dec. 25, 1990
4,979,957
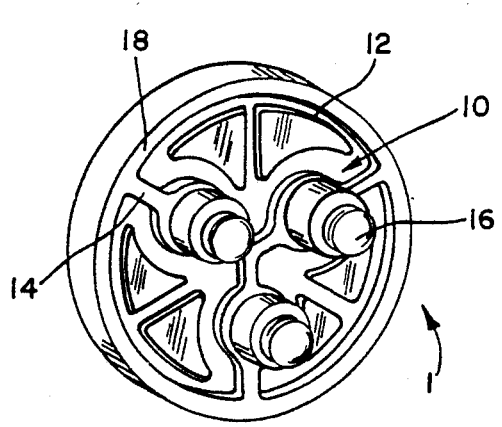
FIG. 1
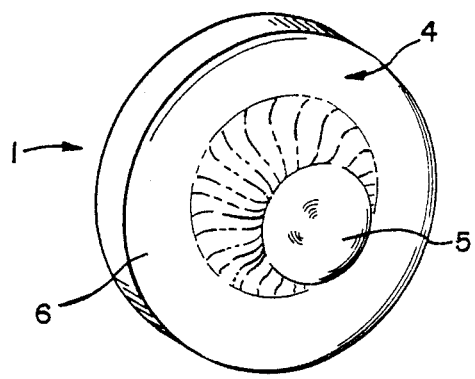
FIG. 2
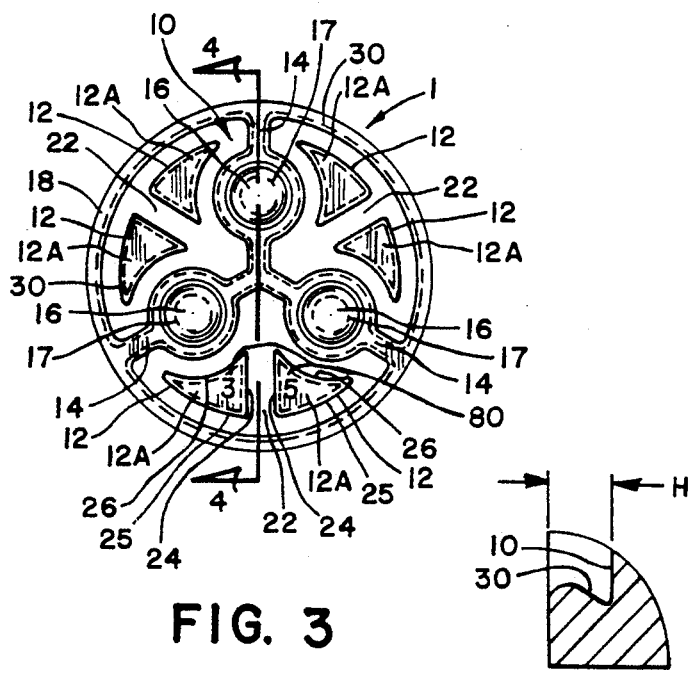
FIG. 3
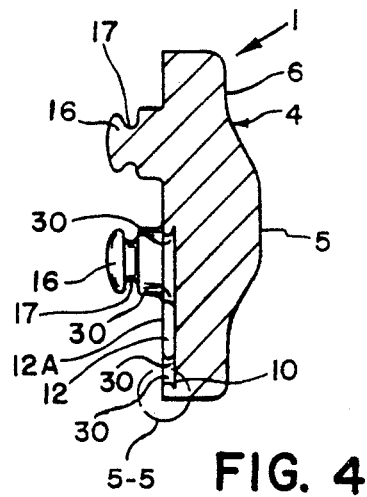
FIG. 4
FIG. 5
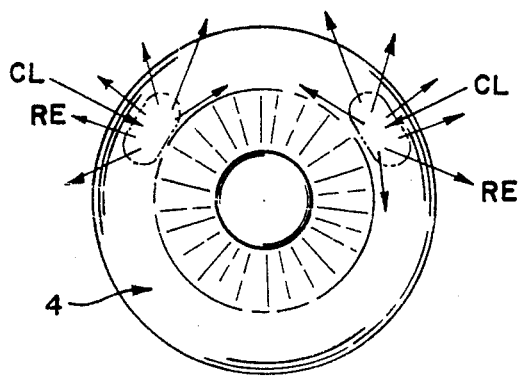
FIG. 6
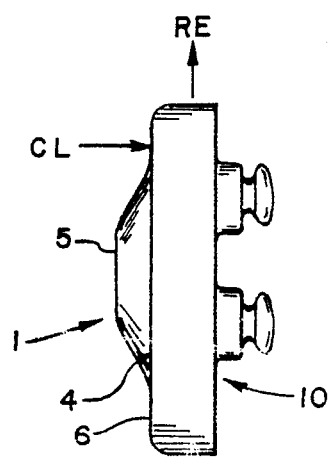
FIG. 7

TEXTURED PROSTHETIC IMPLANT

BACKGROUND OF THE INVENTION

The present invention relates to a prosthetic implant device, and more particularly to such implants including textured surfaces. This invention is particularly suitable for use as a patellar prosthesis or a tibial prosthesis, although it is not limited thereto.

Heretofore, various types of textured surfaces have been incorporated into prosthetic implants. Implants are often affixed into bone with a grouting material, such as a polymeric bone cement. In such cases, various types of texturing of the fixation surfaces of implants have been utilized to enhance the bond or securing between the bone cement and the prosthesis.

Various types of textured or grooved surfaces have been utilized on implants. U.S. Pat. No. 3,728,742 to Averill et al. discloses a knee implant with serrations 32 on the undersurface. U.S. Pat. 3,816,855 to Saleh discloses a knee having short studs 14 on the femoral component and dovetail grooves extending laterally and longitudinally on the undersurface of the tibial component. U.S. Pat. 3,869,731 to Waugh et al. discloses a tibial component of a knee having a lower surface which is generally flat but is formed with two groups of curved rings or ridges 32, 34. U.S. Pat. No. 4,081,866 to Upshaw et al. discloses a knee in which the femoral component includes a serrated face 30 and the tibial component includes serrations 39 and 39' wherein the serrations are provided in a uniform pattern. U.S. Pat. No. 4,215,439 to Gold et al. discloses a knee with cement receiving grooves 44 and niches 46 and 48 in the femoral component and grooves 84 in the tibial component. U.S. Pat. No. 4,714,473 to Bloebaum discloses a knee having femoral and tibial components which include base surfaces which are subdivided by a grid of channels 30 and 40, respectively, which intersect at right angles in a pattern with each channel continuing uninterrupted to a side margin of the component. The channels thus bound a plurality of raised attachment zones. U.S. Pat. No. 4,769,039 to Horber discloses a tibial component with ribs disposed in concentric rings with radially disposed slots. U.S. Pat. No. 4,759,767 to Lacey discloses a tibial component for a knee which includes an extending fin arrangement and a waffle patterned texture on the underside of the component.

OBJECTS OF THE INVENTION

A principal object of this invention is to provide a prosthetic joint implant which provides secure fixation to a bone, especially when bonded thereto with bone cement.

Another object of the invention is to provide a prosthetic implant having a textured undersurface that is designed so that the bone cement can interlock securely to the textured undersurface to prevent subsequent loosening.

A further object of the invention is to provide a textured undersurface for an all polyethylene prosthetic implant which experiences significant compressive loading in the joint, such as with a tibial component or patellar component for a knee prosthesis, such that the textured undersurface is designed to resist expansion or creep of the polyethylene.

A still further object of the invention is to provide a unique and effective texture pattern which provides tensile or life-off resistance.

Another of the invention is to provide a unique and effective texture pattern which provides torque resistance in instances such as a patella, where loading of the patella may produce rotational forces on the implant/cement/bone interface.

SUMMARY OF THE INVENTION

The present invention provides a prosthetic implant which includes a top surface and an undersurface oppositely located therefrom. The undersurface includes a plurality of raised islands with raised rails positioned to separate one or more of the raised islands from other adjacent islands. The implant also includes a raised peripheral rim surrounding the undersurface.

The prosthetic implant of the present invention is particularly suitable for implantation onto a bone surface with bone cement and may be made of ultra high molecular weight polyethylene. Further, the present invention is particularly suitable for use with a joint component which tends to experience significant compressive loading in the joint, such as with a patellar component or a tibial component of a knee prosthesis. Such a polyethylene component is supported by the bone and cement, so that when it experiences the high compressive load, the polyethylene tends to flow or creep. The undersurface design of the present invention is textured so that the bone cement can interlock to the polyethylene undersurface and resist this expansion and potential subsequent loosening. The texture pattern is designed to provide the optimum ratio of cement area to polyethylene area considering the strength of each material. The raised islands are placed in areas where high compressive loads are likely to occur and are "locked in" or surrounded by cement. They are placed more toward the periphery of the undersurface where the most severe loading occurs.

The raised portions of the undersurface are also undercut so that the cement can penetrate "under" the polyethylene and provide tensile or lift-off resistance. This is an important feature since a component such as a patella does experience some tensile forces at this interface. The texture would be rendered useless if it were to lift out of the cement mantle. The height of the raised surfaces (which may suitably be about 1 mm) must be sufficient to provide adequate cement interlock to resist tensile forces.

The raised rails which may include posts extending therefrom, enhance tensile resistance. In the case of a patella, the raised rails may be formed in a radial pattern and provide additional torque resistance. The patella is often loaded more heavily on one side than the other as it glides, producing rotational forces on the implant/cement/bone interface. The radial rails help resist these rotational forces.

BRIEF DESCRIPTION OF THE DRAWINGS

These features and objects of the invention, as well as others, will become apparent to those skilled in the art by referring to the accompanying drawings:

FIG. 1 is a perspective view of the undersurface of a patellar component according to the present invention;

FIG. 2 is a perspective view of the top surface of the patellar component of FIG. 1;

FIG. 3 is bottom plan view of the undersurface of the patellar component of FIG. 1;

FIG. 4 is a cross-sectional view of the patellar component taken along lines 4—4 of FIG. 3;

FIG. 5 is an enlarged partial view taken at circle 5—5 of FIG. 4;

FIG. 6 is a top plan view of the top surface of the patellar component of FIG. 1; and FIG. 7 is a side elevational view of the patellar component of FIG. 1.

DETAILED DESCRIPTION OF THE INVENTION

FIGS. 1-7 illustrate a particularly advantageous embodiment of a textured prosthetic implant according to the present invention. The invention will be described with reference to a patellar prosthetic implant and is particularly suitable as such. However, it is understood that the principles of the invention may be suitable for other implants, especially those that may be subjected to compressive loading, such as a tibial component, as well as others.

It is noted that FIGS. 6 and 7 illustrate an example of the compressive loading that can occur on a patellar prosthesis. This compressive loading is designated by the inwardly directed arrow in each FIG. 6 and 7 labeled "CL". Representative areas under compressive loading are indicated by the phantom lines in FIG. 6. The tendency of a polyethylene component to "flow" or "creep" when it experiences a high compressive load is designated by the outwardly directed arrow labeled "RE" which stands for radial expansion.

The patellar prosthesis of FIGS. 1-7 includes a top surface 4 and an undersurface 10 oppositely located from the top surface 4. The top surface 4 may be any suitable articulating surface, such as that shown, which includes a central raised portion 5 and surrounding contact area 6. The undersurface 10 is provided with a unique texturing in order to provide enhanced, secure fixation to the bone cement and bone surface that is being replaced. The undersurface 10 includes a raised peripheral rim 18 surrounding the undersurface 10, and further includes a plurality of raised islands 12 located on the undersurface 10 within the peripheral rim 18. The undersurface further includes at least one raised rail 14 extending from the peripheral rim 18 to between two of the plurality of islands 12. In the advantageous embodiment of the patellar implant 1 illustrated, the undersurface is substantially circular and includes three raised rails 14 arranged radially and extending from the substantially circular peripheral rim 18 to and meeting at the center of the circular undersurface 10. The plurality of islands 12 may be arranged as pairs of islands (as shown in FIG. 3) with each pair of islands 12 separated from the next adjacent pair of islands 12 by a raised radial rail 14 therebetween. Alternatively, the plurality of islands 12 may be arranged as single islands (not shown) each separated from the next adjacent island 12 by a raised radial rail 14 or as groups of three or more islands (not shown) with each such group separated from the next adjacent group by a raised radial rail 14.

The undersurface 10 is substantially flat. The height "H" as shown in FIG. 5 of the raised rim 18, the plurality of raised islands 12 and the raised rails 14 is approximately the same. A suitable height of these raised textured portions is about one millimeter (1mm). The inner edge of the peripheral rim 18, the outer edge of the plurality of islands 12, and the outer edge of the rails 14 are all undercut to provide a secure interlock of the bone cement (not shown) under the surfaces. The undercut 30 is shown by the dotted lines on the above-indicated edges as shown in FIG. 3 and also as shown in the enlarged cross-sectional portion of FIG. 5.

As mentioned above, and as shown in FIG. 3, the plurality of islands 12 may advantageously be arranged in pairs of islands 12. FIG. 3 shows three pairs of islands or six islands 12. Each pair of islands 12 has an aisle 22 separating each member of the pair. Each pair of islands is separated from adjacent pairs of islands by a raised radial rail 14 therebetween. There are three raised rails 14, as shown in FIG. 3, which each connect to the raised peripheral rim 18 and meet at the center of the undersurface 10. These three radial rails 14 are uniformly positioned about the undersurface 10 at 120° from each other. The aisle 22 between the two members of each pair of islands 12 is located or aligned to be radially opposite from one of the radial rails 14.

Each island 12 includes three distinct sides, a first side 24, second side 25, and third side 26. The first side 24 of each island 12 is substantially straight. The first sides 24 of both islands 12 of a pair face each other and are substantially parallel to each other and are separated by an aisle 22 therebetween.

Each of the rails 14 includes a protruding, elongated post 16 extending from each respective rail. The posts 16 each include a groove 17 thereabout to further enhance the interlock of the bone cement. Each post 16 is substantially circular in cross-section. The respective rail 14, from which each respective post 16 extends, surrounds said respective post 16 on all sides of the post 16 as shown in FIG. 3.

The second side 25 of each island 12 faces the circular peripheral rim 18 and is substantially parallel thereto. The third side 26 of each island 12 faces one of the posts 16 and is substantially parallel thereto. Each of the raised islands 12 includes an enlarged surface area 12A which is substantially flat.

With reference to FIG. 3, it is noted that indicia 80 may be utilized on the enlarged surface area 12A on one or more of the islands 12. In the embodiment shown, a "3" is shown on one island 12 and a "5" on an adjacent island. These numbers "3" and "5" are very slightly recessed numbers on surfaces 12A. The "3" and "5" identify this particular patellar implant as a 35 mm diameter patellar implant. Multiple or other component sizes may be utilized and thus the appropriate size reference may be referenced via the appropriate indicia. Other information, if needed, could be indicated in a similar manner.

The patellar component 1 may be molded or machined out of ultra high molecular weight polyethylene, although other suitable materials and manufacturing means could be utilized, as appropriate.

The prosthetic implant 1 of the present invention described herein includes a unique textured pattern on the undersurface thereof which is designed to enhance and maximize the fixation of the component to the bone cement material which is utilized to secure the component to the bone. While this invention has been described and exemplified, in terms of a particularly advantageous embodiment, those skilled in the art can appreciate that modifications can be made without departing from the spirit and scope of this invention.

I claim:

1. A prosthetic implant having a top surface and an undersurface oppositely located from the top surface, the undersurface having a raised peripheral rim extending from and surrounding the undersurface, and a plurality of groups of raised islands located on the undersurface within the peripheral rim, and wherein each group of raised islands includes at least one individual raised island within each group, and wherein each group of islands is separated from the next adjacent group of islands by a raised elongated rail extending therebetween, and connecting to the raised peripheral rim, and wherein the height of the raised rim, and of each of the individual raised islands, and of each of the raised elongated rails is approximately the same.

2. The implant of claim 1 wherein the height is about 1 mm.

3. The implant of claim 1 wherein the peripheral rim has an inner edge and each of the individual raised islands has an outer edge and wherein the inner edge of the peripheral rim and the outer edge of each of the individual raised islands is undercut.

4. The implant of claim 1 wherein the peripheral rim has an inner edge and each of the individual raised islands has an outer edge and each of the raised elongated rails has an outer edge and wherein the inner edge of the peripheral rim, the outer edge of each of the individual raised islands, and the outer edge of each of the raised elongated rails are all undercut.

5. The implant of claim 1 wherein the implant is manufactured from ultra high molecular weight polyethylene.

6. The implant of claim 1 wherein the undersurface is substantially flat.

7. The implant of claim 1 wherein the peripheral rim of the implant is substantially circular.

8. The implant of claim 7 wherein the undersurface includes at least two raised radial rails which extend from the raised peripheral rim and meet at the center of the undersurface.

9. The implant of claim 7 wherein the undersurface includes three raised radial rails which extend from the raised peripheral rim and meet at the center of the undersurface.

10. The implant of claim 9 wherein the three radial rail are uniformly positioned about the undersurface at 120° from each other.

11. A prosthetic implant having a top surface and an undersurface oppositely located from the top surface, the undersurface having a raised peripheral rim extending from and surrounding the undersurface, and a plurality of groups of raised islands located on the undersurface within the peripheral rim, and wherein each group of raised islands includes at least one individual raised island within each group, and wherein each group of islands is separated from the next adjacent group of islands by a raised elongated rail extending therebetween, and connecting to the raised peripheral rim, and wherein the peripheral rim of the implant is substantially circular, and wherein the undersurface includes three raised radial rails which extend from the raised peripheral rim and meet at the center of the undersurface, and wherein the implant includes three groups of islands, with each group of islands having two individual raised islands therein, with each group separated from the next adjacent group of islands by one of the radial rails therebetween.

12. The implant of claim 15 wherein the two individual raised islands within each of the three groups of islands are spaced apart from each other by a nonraised aisle and wherein each respective nonraised aisle is located or aligned to be radially opposite from one of the radial rails.

13. The implant of claim 11 wherein each of the two individual raised islands within each group includes a first side which is substantially straight and wherein the first sides of both islands within each group face each other and are substantially parallel to each other and are spaced apart from each other.

14. A prosthetic implant having a top surface and an undersurface oppositely located from the top surface, the undersurface having a substantially circular, raised peripheral rim surrounding the undersurface, and a plurality of raised islands located on the undersurface within the peripheral rim, and wherein the plurality of islands are arranged in paris and wherein there are three pairs of islands, and wherein the undersurface includes three raised radial rails extending from the raised peripheral rim and meeting at the center of the undersurface, with each pair of islands separated from the next adjacent pair of islands by one of the radial rails therebetween, and wherein each island includes three distinct sides, and wherein each island includes a first side which is substantially straight and wherein the first sides of both islands of a pair face each other and are substantially parallel to each other and are spaced apart from each other, and wherein each rail includes a protruding, elongated post extending from each respective rail.

15. The implant of claim 14 wherein each post is substantially circular in crosssection, and wherein the respective rail from which each respective post extends, surrounds said respective post on all sides.

16. The implant of claim 14 wherein each island includes a second curved side which faces the circular peripheral rim and is substantially parallel to the rim.

17. The implant of claim 15 wherein each island includes a third curved side which faces one of said posts and is substantially parallel to the one of said posts.

18. The prosthetic implant of claim 1 wherein each of the individual raised islands includes an enlarged surface area which is substantially flat.

19. A prosthetic implant having a top surface and an undersurface oppositely located from the top surface, the undersurface having a raised peripheral rim extending from and surrounding the undersurface, and a plurality of groups of raised islands located on the undersurface within the peripheral rim, and wherein each group of raised islands includes at least one individual raised island within each group, and wherein each group of islands is separated from the next adjacent group of islands by a raised elongated rail extending therebetween, and connecting to the raised peripheral rim, and wherein each of the individual raised islands includes an enlarged surface area which is substantially flat, and wherein a size reference for the prosthesis is indicated on the enlarged surface area of at least one of the individual raised islands.

20. A prosthetic implant having a top surface and an undersurface oppositely located from the top surface, the undersurface having a raised peripheral rim surrounding the undersurface, and a plurality of raised islands located on the undersurface within the peripheral rim, and wherein the plurality of islands are arranged in pairs and wherein there are at least two pairs of islands, with each pair of islands separated from the next adjacent pair of islands by a raised elongated rail extending therebetween and connecting to the raised peripheral rim, and wherein each rail includes a protruding, elongated post extending from each respective rail.

21. A prosthetic implant having atop surface and an undersurface oppositely located from the top surface, the undersurface having a raised peripheral rim surrounding the undersurface, and a plurality of groups of raised islands located on the undersurface within the peripheral rim, and wherein each group of raised islands includes at least one individual raised island within each group, and wherein each group of islands is separated from the next adjacent group of islands by a raised elongated rail extending therebetween, and connecting to the raised peripheral rim, and wherein each rail includes a protruding, elongated post extending from each respective rail.

22. A prosthetic implant having a top surface and an undersurface oppositely located from the top surface, the undersurface having a plurality of groups of raised islands located on the undersurface, and wherein each group of raised islands includes at least one individual raised island within each group, and wherein each group of islands is separated from the next adjacent group of islands by a raised elongated rail extending therebetween, and wherein each rail includes a protruding, elongated post extending from each respective rail.

* * * * *